(12) United States Patent
Ku et al.

(10) Patent No.: US 7,244,852 B2
(45) Date of Patent: Jul. 17, 2007

(54) PROCESS FOR PREPARING 2-METHYLPYRROLIDINE AND SPECIFIC ENANTIOMERS THEREOF

(75) Inventors: Yi-Yin Ku, Buffalo Grove, IL (US); Marlon D. Cowart, Round Lake Beach, IL (US); Padam N. Sharma, Manlius, NY (US)

(73) Assignee: Abbott Laboratories, Abbott Park, IL (US)

( * ) Notice: Subject to any disclaimer, the term of this patent is extended or adjusted under 35 U.S.C. 154(b) by 383 days.

(21) Appl. No.: 10/789,106

(22) Filed: Feb. 27, 2004

(65) Prior Publication Data

US 2004/0260100 A1 Dec. 23, 2004

Related U.S. Application Data

(60) Provisional application No. 60/450,480, filed on Feb. 27, 2003.

(51) Int. Cl.
*C07D 207/04* (2006.01)
(52) U.S. Cl. ....................... 548/570; 548/400
(58) Field of Classification Search ................ 548/400, 548/570
See application file for complete search history.

(56) References Cited

U.S. PATENT DOCUMENTS 6,822,101 B2 * 11/2004 Ku et al. .................... 548/525
6,900,337 B2 * 5/2005 Manzer et al. .............. 548/554

FOREIGN PATENT DOCUMENTS

WO 02/074758 9/2002

OTHER PUBLICATIONS

Ackermann et al., "12. Approaches to the Synthesis of Cytochalasans. Part 9¹) A Versatile Concept Leading to All Structural Types of Cytochalasans," Helvetica Chimica Acta 73(1):122-132 (1990).

Andres et al., "A simple stereoselective synthesis of enantiopure 2-substituteed pyrrolidines and piperidines from chiral (R)-phenylglycinol-derived bicyclic 1,3-oxazolidines," Eur. J. Org. Chem. 1719-1726 (2000).

Donner et al., "Conversion of chiral amino acids to enantiomerically pure α-methylamines," Tetrahedron Letters 36(8):1223-1226 (1995).

Elworthy et al., "The configurational stability of chiral lithio α-amino carbanions. The effect of Li-O vs. Li-N complexation." Tetrahedron 50(20):6089-6096 (1994).

Gaffield et al., "Chiroptical properties of n-nitrosopyrrolidines and n-nitrosamino acids," Tetrahedron 37:1861-1869 (1981).

Karlsson et al., "Binding of peptides in solution by the *Escherichia coli* chaperone PapD as revealed using an inhibition ELISA and NMR spectroscopy," Bioorganic & Medicinal Chemistry 6:2085-2101 (1998).

Karrer et al., "270. Conversion of optically active α-amino carboxylic acids into optically active amines with identically carbon structures," Helv. Chim. Acta 34:2202-2210 (1951).

Kunoi et al., "Asymmetric induction in the [2,3] sigmatropic rearrangement via chiral ammonium ylides," Chemistry Letters 1077-1080 (1980).

Marshall et al., "Synthesis of 7(8)-desoxyasperdiol. A precursor of the cembranoid asperdiol," J. Org. Chem. 51:858-863 (1986).

Nijhuis et al., "Sterochemical aspects of the "*tert*-amino effects". 2. Enantio-and diastereoselectivity in the synthesis of quinolines, pyrrolo[1,2-α]quinolines, and [1,4]oxazino[4,3-α]quinolines," J. Org. Chem. 54:209-216 (1989).

Olah et al., "Synthetic methods and reactions. 112. Synthetic transformations with trichlormethylsilane/sodium iodide reagent," J. Org. Chem. 48:3667-3672 (1983).

Yamada et al., "A biogenetic-type asymmetric cyclization syntheses of optically active α-cyclocitral and *trans*-α-damascone," Tetrahedron Letters 5:381-384 (1973).

* cited by examiner

*Primary Examiner*—Golam M. M. Shameem
(74) *Attorney, Agent, or Firm*—Portia Chen

(57) ABSTRACT

The invention relates to a process for preparing 2-methylpyrrolidine and, more particularly, specific enantiomers of 2-methylpyrrolidine. Novel intermediates also are described.

2 Claims, No Drawings

PROCESS FOR PREPARING 2-METHYLPYRROLIDINE AND SPECIFIC ENANTIOMERS THEREOF

This application claims priority to U.S. patent application Ser. No. 60/450,480, filed Feb. 27, 2003, incorporated herein by reference.

BACKGROUND OF THE INVENTION

1. Technical Field of the Invention

The present invention relates to a process for preparing 2-methylpyrrolidine compounds, specific enantiomers, and derivatives thereof. More particularly, the invention relates to a process for preparing a specific isomer of 2-methylpyrrolidine from a chiral starting material.

2. Description of the Related Technology

Pyrrolidine ring systems and their derivatives often are present in many biologically important substances. 2-Methylpyrrolidine, in particular, is a compound useful as a starting material in various pharmaceutical processes. For example, 2-methylpyrrolidine has demonstrated usefulness as a starting material in the preparation of $H_3$ receptor ligands. International Publication WO 02/074758, published Sep. 26, 2002, describes the preparation of cyclic amines attached to a benzofliran moiety via an alkyl chain. Such compounds have demonstrated beneficial effects for treatment of $H_3$-mediated conditions or diseases, for example, cognitive function or obesity, among other conditions and diseases.

Processes for preparing 2-methylpyrrolidine have been reported in the literature. For example, Elworthy, et al. report in Tetrahedron, Vol. 50, No. 20, pp. 6089–6096 (1994) a process for preparing 2-methylpyrrolidines via the alkylation of α-lithio pyrrolidine derivatives. Andres, et al. describe in Eur. J. Org. Chem., pp. 1719–1726 (2000) the removal of an N-benzyl moiety by hydrogenolysis over palladium on carbon and treatment with tosyl chloride of (2R)-2-[(2'R)-2'-methyl-N-pyrrolidinyl]-2-phenyl-1-ethanol. Nijhuis, et al. suggest in J. Org. Chem., Vol. 54, No. 1, pp. 209–216 (1989) that optically active pyrrolidines can be prepared from prolinol via a salt of 2-chloromethyl(pyrrolidine). In addition, Donner, et al. describe a process for preparing enantiomerically pure 2-methylpyrrolidine via Raney nickel reduction of a N-Boc-protected prolinol thioether derivative in Tetrahedron Letters, Vol. 36, No. 8, pp. 1223–1226 (1995). Although these methods can provide optically active pyrrolidine derivatives under some conditions, the preparation of compounds via such processes in large quantities generally is not optimally cost-effective for commercial utility.

Accordingly, significant reliance on methods of resolving racemic 2-methylpyrrolidine to obtain a single desired enantiomer exists in the pharmaceutical industry. For example, racemic mixtures have been resolved by forming diastereomeric salts with a chiral acid, such as tartaric acid. (See, for example, Elworthy, et al., Tetrahedron, Vol. 50, No. 20, pp. 6089–6096 (1994)). Racemic mixtures also have been separated by the attachment of a mixture of enantiomers to a chiral auxiliary, separation of the resulting mixture of diastereomers by recrystallization or chromatography, and optional liberation of the optically pure product from the auxiliary as described in Furniss, Hannaford, Smith, and Tatchell, "Vogel's Textbook of Practical Organic Chemistry", 5th edition (1989); and Longman Scientific & Technical, Essex CM20 2JE, England. In addition, direct separation of a mixture of optical enantiomers on chiral chromatographic columns or by fractional recrystallization also has been a commonly employed in the art. Unfortunately, these methods often result in the inefficient use and undue waste of valuable starting materials, which render such processes less effective for commercially viable processes for preparing an optically active compound.

Accordingly, it would be beneficial to provide an efficient, cost-effective synthesis of 2-methylpyrrolidine. In addition, it would be beneficial to provide a process for obtaining a specific enantiomer of 2-methylpyrrolidine via such efficient, cost-effective synthesis.

SUMMARY OF THE INVENTION

The invention comprises a process for preparing 2-methylpyrrolidine and, more specifically, a particular enantiomer of 2-methylpyrrolidine obtained from a chiral starting material. The chiral starting material is a commercially obtained prolinol compound, commonly obtained either as (R)-prolinol or (S)-prolinol. Use of the prolinol starting material affords an effective process for the synthesis of 2-methylpyrrolidine and its specific enantiomers, for example the preparation of 2-(R)-methylpyrrolidine and 2-(S)-methylpyrrolidine from (S)-prolinol and (R)-prolinol, respectively.

In one aspect, the invention comprises a process for preparing a compound of formula (V):

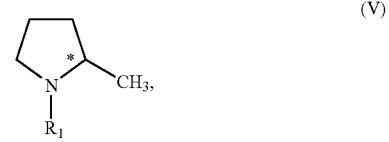

wherein * denotes a chiral center that can be designated a R— or S-stereocenter, $R_1$ is hydrogen or a nitrogen-protecting group ($R_p$), or a salt thereof, comprising the steps of:

1a) providing a compound of formula (II):

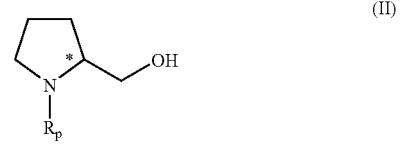

wherein * is as previously defined and $R_p$ is a nitrogen-protecting group;

1b) treating a compound of formula (II) with a sulfonylating reagent to obtain a compound of formula (III):

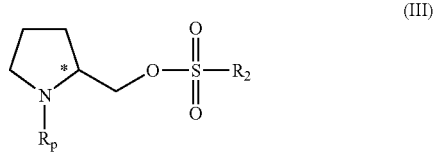

wherein * and $R_p$ are as previously defined and $R_2$ is an unsubstituted alkyl, substituted alkyl, unsubstituted aryl, or substituted aryl group;

1c) reacting the —O—S(O)$_2$—R$_2$ group in a compound of formula (III) with an alkali metal triethylborohydride to obtain a desired enantiomer of a compound of formula (V):

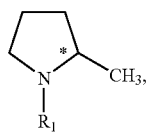

(V)

wherein * and R$_1$ are as previously defined. In one embodiment of the invention, the —O—S(O)$_2$—R$_2$ group of compound (III) can be removed using lithium triethylborohydride reagent to provide a compound of formula (V). The N-protected prolinol compound of formula (II) can be purchased from a commercial vendor or, alternatively, a desired enantiomer of prolinol having the formula (I):

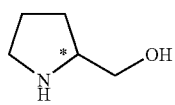

(I)

can be reacted with an amine-protecting reagent to provide a compound of formula (II).

In another aspect, the invention comprises a process for preparing a compound of formula (V):

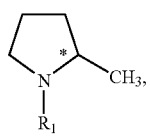

(V)

wherein * denotes a chiral center that can be designated a R— or S-stereocenter, R$_1$ is hydrogen or a nitrogen-protecting group, or a salt thereof, comprising the steps of:
2a) providing a compound of formula (III):

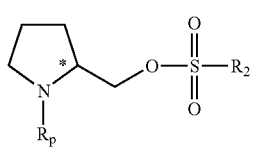

(III)

wherein * is as previously defined, R$_p$ is a nitrogen-protecting group, and R$_2$ is an unsubstituted alkyl, substituted alkyl, unsubstituted aryl, or substituted aryl group, and treating the compound of formula (III) with an alkali metal iodide salt to obtain a compound of the formula (IV):

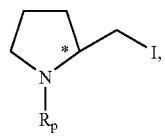

(IV)

wherein * and R$_p$ are as defined for a compound of formula (III); and
2b) hydrogenating the compound of formula (IV) to obtain a desired enantiomer of a compound of formula (V):

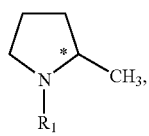

(V)

wherein * and R$_1$ are as previously defined. The preferred iodide salt is a metal iodide salt. Alternatively, the compound of formula (IV) can be directly prepared from a compound of formula (II), as previously described, by reacting a compound of formula (II) with an iodine reagent, for example dimeric iodine (I$_2$), an alkali metal iodide salt, or a tetraalkylammonium iodide salt.

Compounds of formula (V), wherein R$_1$ is a nitrogen-protecting group, can be deprotected under conventional conditions to provide a desired 2-methylpyrrolidine compound, which can be further treated to provide a desired salt or other suitable derivative under conditions well-known to those with skill in the art.

Novel intermediates prepared using processes of the invention also are contemplated.

DETAILED DESCRIPTION OF THE INVENTION

Definition of the Terms

A number of terms are used herein to designate particular elements of the present invention. When so used, the following meanings are intended:

The term "alkyl" as used herein, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. The alkyl groups of the invention can be substituted with 0, 1, 2, 3, 4, or 5 halo substituents.

The term "aryl" as used herein, refers to a monocyclic aromatic ring system containing six carbon atoms. Representative examples of aryl include, but are not limited to, phenyl. The aryl groups of this invention are substituted with 0, 1, 2, 3, 4, or 5 substituents independently selected from acyl, acyloxy, alkenyl, alkoxy, alkoxyalkoxy, alkoxyalkyl, alkoxycarbonyl, alkoxyimino, alkoxysulfonyl, alkyl, alkylsulfonyl, alkynyl, amido, carboxy, cyano, formyl, haloalkoxy, haloalkyl, halo, hydroxy, hydroxyalkyl, mercapto, nitro, and thioalkoxy.

When used to refer to an "alkali metal triethylborohydride", the term "alkali metal" refers to lithium, sodium, and potassium, for example as in lithium triethylborohydride, sodium triethylborohydride, and potassium triethylborohydride.

The term "iodine reagent" as used herein, refers to a reagent capable of introducing iodine, for example I$_2$ or an alkali metal iodide salt.

The term "iodide salt" as used herein, refers to alkali metal iodide salts, for example, lithium iodide, sodium iodide, potassium iodide, and cesium iodide.

The term "nitrogen-protecting group" as used herein, refers to those groups intended to protect a nitrogen atom against undesirable reactions during synthetic procedures. Nitrogen-protecting groups comprise carbamates, amides, N-benzyl derivatives, and imine derivatives. Preferred nitrogen-protecting groups are acetyl, benzoyl, benzyl, benzyloxycarbonyl (Cbz), formyl, phenylsulfonyl, pivaloyl, tert-butoxycarbonyl (Boc), tert-butylacetyl, and triphenylmethyl (trityl). Nitrogen-protecting groups can be appended onto amino groups in compounds of the invention by reacting the amine group with a base, for example triethylamine, and an amine-protecting reagent. The amine-protecting reagent provides a suitable nitrogen-protecting group and can be, but need not be, selected from an alkyl halide, an alkyl triflate, a dialkylcarbonic anhydride, for example as represented by (alkyl-O)$_2$C=O or di-tert-butyl dicarbonate, a diarylcarbonic anhydride, for example as represented by (aryl-O)$_2$C=O, an acyl halide, an alkylchloroformate, for example isobutylchloroformate, an arylchloroformate, for example phenylchloroformate, an alkylsulfonyl halide, for example methanesulfonyl chloride, a haloalkylsulfonyl halide, for example trifluoromethanesulfonyl chloride, an arylsulfonyl halide, or halo-CON(alkyl)$_2$, for example pyrrolidine-1-carbonyl chloride, acetylchloride, benzoylchloride, a benzylic halide such as benzylbromide, benzyloxycarbonylchloride, formylfluoride, phenylsulfonylchloride, pivaloylchloride, di-tert-butyl dicarbonate, trifluoroacetic anhydride, and triphenylmethylchloride.

The term "sulfonylating reagent" as used herein, refers to a reagent that can be reacted with an alcohol or an amine to give a sulfonate or sulfonamide. Examples of sulfonating reagents can include, for example, alkylsulfonyl halides, such as methanesulfonyl chloride, alkyl sulfonic anhydrides, such as methansulfonic anhydride, haloalkylsulfonic anhydrides, such as trifluoromethanesulfonic anhydride, arylsulfonyl halides, such as para-toluenesulfonyl chloride, and arylsulfonic anhydrides, such as para-toluenesulfonic anhydride.

EMBODIMENTS OF THE INVENTION

The invention provides processes for preparing a 2-methylpyrrolidine compound, which is a useful compound and an intermediate for preparing pharmaceutical products. The invention comprises processes for preparing 2-methylpyrrolidine in an efficient manner, suitable for preparing a single enantiomer, for example the R— and S-enantiomers. These stereoisomers are "R" or "S" depending on the configuration of substituents around the chiral carbon atom. The terms "R" and "S" used herein are configurations as defined in the IUPAC 1974 Recommendations for Section E, Fundamental Stereochemistry, Pure Appl. Chem., 1976, 45:13–30.

Examples of processes of the invention follow in Schemes, which are intended to illustrate processes the invention and are not meant to limit the scope of the invention in any way. As shown below, methods for preparing the R-enantiomer of 2-methylpyrrolidine from (S)-prolinol are shown. Isomeric forms of the compounds described in the Schemes are contemplated and considered as encompassed within the scope of the claimed invention, which also allows for preparation of the S-isomer.

Processes for preparing 2-(R)-methylpyrrolidine are exemplified in Scheme 1, below.

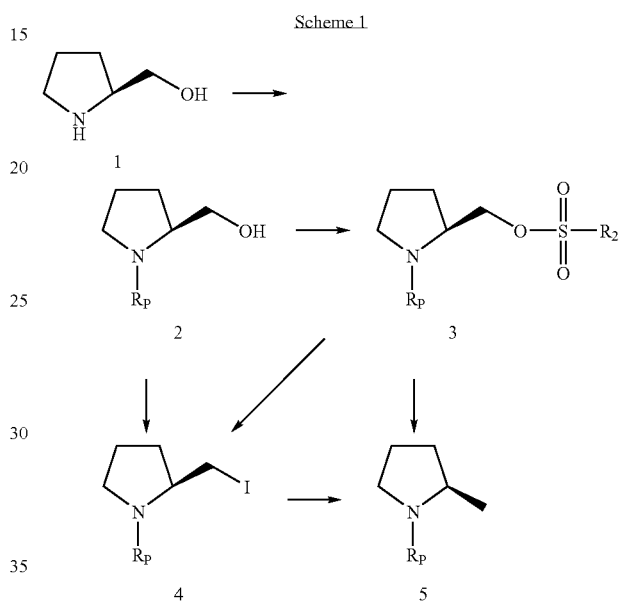

Scheme 1

As shown in Scheme 1, a commercially available (S)-prolinol (or (S)-2-pyrrolidinemethanol, Chemical Abstracts number 23356-96-9) (1), can be reacted with an amine-protecting reagent in the presence of an inorganic or organic base to provide a N-protected-(S)-prolinol derivative (2). However, the N-protected-(S)-prolinol derivative (2) also can be obtained from a commercial vendor, for example, Sigma-Aldrich Chemical Company in St. Louis, Mo., USA. The N-protected-(S)-prolinol (2) is treated with a sulfonylating reagent in the presence of an organic base to provide an N-protected-2-(alkyl- or aryl)sulfonate ester of (S)-prolinol (3). The N-protected-2-(alkyl- or aryl)sulfonate ester of (S)-prolinol (3) is reacted with a metal iodide salt to provide the N-protected-2-(S)-iodomethylpyrrolidine (4), which also can be prepared directly from the N-protected-(S)-prolinol (2) by reacting the N-protected-(S)-prolinol (2) with I$_2$, an alkali metal iodide salt, or a tetraalkylammonium iodide salt. The N-protected-2-(S)-iodomethylpyrrolidine (4) can be hydrogenated using a palladium catalyst reaction to provide N-protected-2-(R)-methylpyrrolidine (5).

In another aspect, the N-protected-2-(alkyl- or aryl)sulfonate ester of (S)-prolinol (3) is treated with alkali metal triethylborohydride, for example LiBH(Et)$_3$, to directly afford the N-protected-2-(R)-methylpyrrolidine (5). The N-protected-2-(R)-methylpyrrolidine can be treated with suitable reducing agents to remove the N-protecting group using conventional procedures known in the art to provide 2-(R)-methylpyrrolidine or a salt thereof, or other suitable derivatives.

It will be clear to one with skill in the art that the processes of invention, as described by the Schemes and detailed description provided herein, would be suitable for preparing the corresponding S-enantiomer of any of the compounds and intermediates described by the Schemes or the Examples. For example, in any process as shown in Scheme 1, (R)-prolinol can be substituted for the (S)-prolinol starting material to provide a corresponding N-protected-2-(S)-methylpyrrolidine compound (5). Such substitution would be within the purview of one with skill in the art and could be readily accomplished without undue experimentation.

The N-protected-(S)-prolinol, wherein $R_p$ is a nitrogen-protecting group, can be directly obtained from a commercial vendor, for example, Sigma-Aldrich Chemical Company, St. Louis, Mo., USA or Fisher Scientific International Inc., Hampton, N.H., USA. Alternatively, as shown in Scheme 1, the N-protected-(S)-prolinol (2) can be prepared by reacting the amine group of the (S)-prolinol (1) with any suitable amine-protecting reagent.

In accordance with Scheme 1, (S)-prolinol is reacted with an amine-protecting reagent to provide an N-protected-(S)-prolinol (2). (S)-prolinol is a commercially available amino alcohol, which can be obtained from Sigma-Aldrich Chemical Company and/or Fisher Scientific International Inc. The amine-protecting reagent can provide any one of many commonly available nitrogen-protecting groups, or a mixture thereof. Typical nitrogen-protecting groups for $R_p$ include, but are not limited to, acetyl, benzoyl, benzyl, benzyloxycarbonyl (Cbz), formyl, phenylsulfonyl, pivaloyl, tert-butoxycarbonyl (Boc), tert-butylacetyl, trifluoroacetyl, and triphenylmethyl (trityl). The preferred nitrogen-protecting groups are benzyloxycarbonyl and tert-butoxycarbonyl.

Typically, the reaction is carried out in the presence of an organic base. Although most bases are suitable, an organic base, for example an amine, is preferred. Such bases can include, but are not limited to, N,N-dimethylaminopyridine, pyridine, triethylamine, diisopropylethylamine, N,N-dimethylaniline, trimethylamine, triisopropylamine, and the like, or a mixture thereof. Preferred bases are triethylamine and pyridine. The amine-protecting reagent can include, is not limited to, an alkyl halide, an alkyl triflate, a dialkylcarbonic anhydride, for example as represented by (alkyl-O)$_2$C=O, a diarylcarbonic anhydride, for example as represented by (aryl-O)$_2$C=O or di-tert-butyl dicarbonate, an acyl halide, an alkylchloroformate, for example isobutylchloroformate, an arylchloroformate, for example phenylchloroformate, an alkylsulfonylhalide, for example methanesulfonyl chloride, a haloalkylsulfonylhalide, for example trifluoromethanesulfonylchloride, an arylsulfonylhalide, an alkanoyl halide, a benzylic halide, or halo-CON(alkyl)$_2$. More particularly, examples of amine-protecting reagents include, but are not limited to, for example acetylchloride, benzoylchloride, benzylbromide, benzyloxycarbonylchloride, formylfluoride, pyrrolidine-1-carbonyl, phenylsulfonylchloride, pivaloylchloride, di-tert-butyl dicarbonate (or tert-butoxycarbonyl anhydride), trifluoroacetic anhydride, and triphenylmethylchloride. Preferably, the reaction is carried out at or below room temperature in any suitable solvent. Examples of preferred solvents include, but are not limited to, aprotic solvents including, but not limited to, methylene chloride, diethyl ether, acetone, acetonitrile, tetrahydrofuran, methyl-tert-butyl ether, and ethyl acetate. Less polar aprotic solvents, for example ethyl acetate, are preferred. A further discussion of nitrogen-protecting groups and the reagents and solvents in which they are most effective can be found in T. W. Greene and P. G. M. Wuts, *Protective Groups in Organic Synthesis,* 3rd ed., John Wiley & Son, Inc., 1999.

The hydroxy group of the N-protected-(S)-prolinol (2) is reacted with a sulfonylating reagent to afford an N-protected-2-(alkyl- or aryl)sulfonate ester of (S)-prolinol (3), wherein $R_p$ is as defined above and $R_2$ is unsubstituted alkyl, substituted alkyl, unsubstituted aryl, or substituted aryl. As used herein, the term "alkyl" as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. The alkyl groups of the invention can be substituted with 0, 1, 2, 3, 4, or 5 halo substituents such as for example, chloro and fluoro substituents. Examples of substituted alkyl groups can include, but are not limited to, dichloromethyl, trifluoromethyl, and the like. Examples of preferred alkyl groups for $R_2$ include, but are not limited, methyl and trifluoromethyl (—CF$_3$). The term "aryl" as used herein, means a monocyclic aromatic ring system containing six carbon atoms. Representative examples of aryl include, but are not limited to, phenyl. The aryl groups of this invention are substituted with 0, 1, 2, 3, 4, or 5 substituents independently selected from acyl, acyloxy, alkenyl, alkoxy, alkoxyalkoxy, alkoxyalkyl, alkoxycarbonyl, alkoxyimino, alkoxysulfonyl, alkyl, alkylsulfonyl, alkynyl, amido, carboxy, cyano, formyl, haloalkoxy, haloalkyl, halo, hydroxy, hydroxyalkyl, mercapto, nitro, and thioalkoxy, for example, dimethylphenyl, nitrophenyl, and the like. Preferred aryl groups for $R_2$ are phenyl and alkyl-substituted phenyl groups, for example, -phenyl-CH$_3$ and particularly -phenyl-4-CH$_3$.

The sulfonylating reagent can be any suitable reagent that provides an alkylsulfonyl or an arylsulfonyl group to react with the hydroxy group of the N-protected-(S)-prolinol. Sulfonylating reagents can include, for example, alkylsulfonyl halides, alkyl sulfonic anhydrides, haloalkylsulfonic anhydrides, arylsulfonyl halides, and arylsulfonic anhydrides. More particular examples of suitable sulfonylating reagents can include, for example, methanesulfonic anhydride, methanesulfonyl chloride, para-toluenesulfonic chloride, para-toluenesulfonic anhydride, trifluoromethanesulfonic anhydride, and the like. The reaction typically is carried out in the presence of an organic base. Such bases can include, but are not limited to, N,N-dimethylaminopyridine, pyridine, triethylamine, diisopropylethylamine, N,N-dimethylaniline, trimethylamine, triisopropylamine, and the like, or a mixture thereof. Preferred bases are triethylamine and pyridine, and the like, or a mixture thereof. Although a wide variety of solvents are suitable for the reaction, aprotic solvents are well-suited for the reaction. Examples of aprotic solvents include, but are not limited to, methylene chloride (or dichloromethane), diethyl ether, acetone, acetonitrile, tetrahydrofuran, methyl-tert-butyl ether, and ethyl acetate. The preferred solvent is ethyl acetate or methylene chloride.

Typically, the sulfonylating reagent is reacted with the N-protected-(S)-prolinol in a range of from about 1:1 to about 1:5 molar equivalents, relative to the N-protected-(S)-prolinol. preferably, about 3 molar equivalents of sulfonylating reagent are used for each mole of the N-protected-(S)-prolinol. The reaction can be carried out in at least room temperature. The reaction can be accomplished in from about 1 to 2 hours. A further discussion of the reagents and solvents suitable for providing a sulfonyl group to react with a hydroxy moiety can be found in Lee, et al., J. Med. Chem., 44:2015–2026 (2001) and T. W. Greene and P. G. M. Wuts, *Protective Groups in Organic Synthesis*, 3rd ed., John Wiley & Son, Inc., 1999.

The N-protected-2-(alkyl- or aryl)sulfonate ester of (S)-prolinol (3) is treated with an iodide salt to obtain the N-protected-2-(S)-iodomethylpyrrolidine (4), wherein $R_p$ is as previously defined. The iodide salt can be any metal iodide salt. Examples of suitable iodide salts for the reaction can include, but are not limited to, sodium iodide, potassium iodide, cesium iodide, and the like. The iodide salts are commercially available and, typically, can be reacted with the N-protected-2-(alkyl- or aryl)sulfonate ester of (S)-prolinol in any suitable solvent. Preferably, from about 1:1 to about 1:20 molar equivalents of the iodide salt are used relative to the amount N-protected-2-(alkyl- or aryl)sulfonate ester of (S)-prolinol. Typically, the reaction is carried out in any inert solvent in which the starting materials for the reaction can be dissolved. Preferred solvents are polar solvents, for example, ethyl nitrile, acetone, 2-butanone, tetrahydrofuran, and the like. The preferred solvent is tetrahydrofuran.

Alternatively, N-protected-(S)-prolinol (2) can be treated with an iodine reagent to afford N-protected-2-(S)-iodomethylpyrrolidine (4). Typically, the iodine reagent is dimeric iodine ($I_2$) or an alkali metal iodide salt, for example sodium iodide. Tetraalkylammonium iodide salts also can be used, for example tetrabutylammonium iodide. The treatment of the N-protected-(S)-prolinol beneficially can include the use of a phosphine, particularly a triarylphosphine, such as triphenylphosphine, to activate the hydroxy moiety. Wherein the sodium iodide is used, a bromide reagent such as $CBr_4$, also is included as a component of the reaction. The reaction can be carried out in any suitable solvent. Suitable solvents can include, but are not limited to, polar, aprotic solvents, for example, toluene, acetonitrile, acetone, and the like. Examples of suitable conditions for obtaining the N-protected-2-(S)-iodomethylpyrrolidine from N-protected-(S)-prolinol (2) follow in Table 1, below, summarizing the iodine reagent used, typical conditions for the reaction, and a further reference for determining suitable conditions.

TABLE 1

| Iodine Reagent | Conditions | Citation |
| --- | --- | --- |
| $I_2$ | $PPh_3$, toluene/$CH_3CN$, imidazole | J. Org. Chem., 51: 858–863 (1986) |
| NaI | $PPh_3$, $CBr_4$, Acetone | Helv. Chim. Acta, 73 (1): 122–32 (1990) |
| NaI | $MeSiCl_3$ | J. Org. Chem., 48: 3667–3672 (1983) |

The N-protected-2-(S)-iodomethylpyrrolidine (4) can undergo hydrogenolysis to afford the N-protected-2-(R)-methylpyrrolidine (5). Typically, the hydrogenation reaction is carried out using a source of hydrogen and a catalyst. The reaction can be accomplished by using hydrogen gas or by providing hydrogen via a hydrogen donor source, such as ammonium formate, formic acid, benzyltriethylammonium formate, hydrazine, cyclohexadiene, and the like, or a mixture thereof. The catalyst typically is a palladium or platinum catalyst. Examples of suitable catalysts can include, but are not limited to, palladium on carbon, palladium on calcium carbonate, palladium on calcium carbonate, palladium on barium sulfate, palladium acetate, $PdCl_2$, $Pd(OH)_2$, platinum on carbon, $Pt(Cl)_2$, and platinum oxide. The reaction can be accomplished in any suitable solvent, typically a polar organic solvent, in the presence of an organic base, for example an amine, or inorganic base. Examples of polar organic solvents include, but are not limited to, methanol, ethanol, isopropyl alcohol, and the like. The preferred solvent is methanol. A suitable organic base can be selected from N,N-dimethylaminopyridine, pyridine, diisopropylethylamine, N,N-dimethylaniline, triethylamine, triisopropylamine, and the like, or a mixture thereof. The preferred amine is triethylamine.

Also shown in Scheme 1, the N-protected-2-(alkyl- or aryl)sulfonate ester of (S)-prolinol (3) alternatively is treated with an alkali metal triethylborohydride, or other strong reducing agents, to afford the N-protected-2-(R)-methylpyrrolidine (5). Preferred alkali metal triethylborohydride compounds include, but are not limited to, lithium triethylborohydride, sodium triethylborohydride, and potassium triethylborohydride. The preferred alkali metal triethylborohydride is lithium triethylborohydride, which is commonly known as super hydride reagent or L-super hydride. The reaction can be carried out in an inert aprotic solvent. Examples of suitable solvents for the reaction can include, but are not limited to, methylene chloride, diethyl ether, acetonitrile, tetrahydrofuran, and the like, or a mixture thereof. The preferred solvent is tetrahydrofuran. The reaction preferably is carried out at, or below, room temperature. Typically, the amount of reducing agent can be from about 1:1 to about 1:10 molar equivalents relative to the N-protected-2-(alkyl- or aryl)sulfonate ester of (S)-prolinol. The preferred temperature for carrying out the reaction can include from about −20° C. to about 20° C. The preferred temperature is 0° C.

Unless otherwise described, any reagent, catalyst, solvent, or starting material for the reaction can be obtained from a commercial vendor, for example, Sigma-Aldrich Chemical Company in St. Louis, Mo., USA or Fisher Scientific International Inc. in Hampton, N.H. USA. Compounds and intermediates in the processes described can be isolated and purified by methods well-known to those skilled in the art of organic synthesis. Examples of conventional methods for isolating and purifying compounds include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

The foregoing description illustrates processes for preparing N-protected-2-methylpyrrolidine compounds, including N-protected-2-(R)-methylpyrrolidine and N-protected-2-(S)-methylpyrrolidine. The N-protected-2-methylpyrrolidine compounds can be deprotected according to well-known procedures in the art to afford the corresponding 2-methylpyrrolidine compounds. Salts of 2-methylpyrrolidine also can be easily prepared according to procedures commonly available to those with skill in the art. Such procedures are illustrated in Scheme 2, below.

Scheme 2

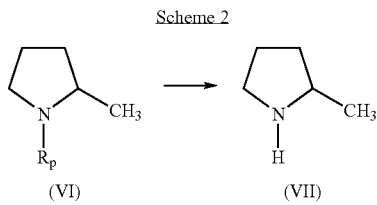

(VI)                    (VII)

As shown in Scheme 2, N-protected-2-methylpyrrolidine (VI), wherein $R_p$ is a nitrogen-protecting group can be deprotected to obtain the corresponding 2-methylpyrrolidine (VII) or a salt thereof.

Compounds of formula (VI) can be readily deprotected by conventional procedures for removing nitrogen-protecting groups. For example, nitrogen-protecting groups can be easily removed by using a strong acid in an inert organic solvent, preferably an aprotic, organic solvent, water, or a mixture thereof. Examples of acids suitable for removing the nitrogen-protecting group can include, but are not limited to, trifluoroacetic acid, para-toluenesulfonic acid, and hydrochloric acid. Suitable solvents can include, for example, ethyl acetate, isopropyl alcohol, methylene chloride, dioxane, dimethylethane, toluene, and the like, or mixtures thereof. Preferred conditions for removing the nitrogen-protecting group, for example, tert-butoxycarbonyl, are treating an N-protected compound with hydrochloric acid in an inert, organic solvent, such as ethyl acetate or dioxane. Further description of the reagents and conditions suitable for removing nitrogen-protecting groups can be found in T. W. Greene and P. G. M. Wuts, *Protective Groups in Organic Synthesis,* 3rd ed., John Wiley & Son, Inc., 1999.

The nitrogen moiety of 2-methylpyrrolidine compounds of the invention can be treated with an acid to form a desired salt. Acceptable salts are well-known in the art. The salts can be prepared in situ during the final isolation and purification of the compounds of the invention or separately by reacting a free base function with a suitable organic acid. For example, a compound may be reacted with an acid at or above room temperature to provide the desired salt, which is deposited, and collected by filtration after cooling. Examples of acids suitable for the reaction include, but are not limited to, trifluoroacetic acid, tartaric acid, lactic acid, succinic acid, hydrochloric acid, and sulfuric acid, as well as mandelic acid, atrolactic acid, methanesulfonic acid, ethanesulfonic acid, toluenesulfonic acid, naphthalenesulfonic acid, carbonic acid, fumaric acid, gluconic acid, acetic acid, propionic acid, salicylic acid, hydrobromic acid, phosphoric acid, citric acid, hydroxybutyric acid, camphorsulfonic acid, malic acid, phenylacetic acid, aspartic acid, glutamic acid, and the like. Preferably, aprotic solvents are used for the preparation of acid addition salts. Examples of such solvents include, but are not limited to, methylene chloride, diethyl ether, acetone, acetonitrile, tetrahydrofuran, methyl-tert-butyl ether, and ethyl acetate, and the like, or a mixture thereof. The preferred solvent is ethyl acetate.

Accordingly, one aspect of the invention relates to preparing a N-protected-2-methylpyrrolidine compound, comprising the steps of:

3a) treating the hydroxy group of an N-protected prolinol, which can be commercially obtained or prepared via reacting prolinol with an amine-protecting group, with a sulfonylating reagent to obtain an N-protected-2-(alkyl- or aryl) sulfonate ester of prolinol; and 3b) reacting the N-protected-2-(alkyl- or aryl)sulfonate ester of prolinol with an alkali metal triethylborohydride, such as lithium triethylborohydride, to obtain N-protected-2-methylpyrrolidine.

Another aspect of the invention relates to preparing a N-protected-2-methylpyrrolidine compound, comprising the steps of:

4a) reacting a N-protected prolinol with an iodine reagent or reacting a N-protected-2-(alkyl- or aryl)sulfonate ester of prolinol with an iodide salt to obtain an N-protected-2-iodomethylpyrrolidine; and 4b) hydrogenating the N-protected-2-iodomethylpyrrolidine to obtain N-protected-2-methylpyrrolidine.

The processes described herein provide useful compounds for preparing compounds demonstrating pharmaceutical activity and, particularly, compounds demonstrating activity for modulating histamine-3 receptors. For example, 2-methylpyrrolidine can be useful for preparing compounds having a cyclic amine attached to a benzofuran moiety as described in International Publication No. WO 02/074758.

Yet still another aspect of the invention relates to a compound of the formula (VIII):

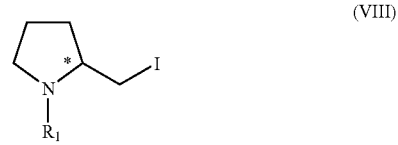

(VIII)

wherein* denotes a chiral center that can be designated as a R— or S-stereocenter and $R_1$ is hydrogen or a nitrogen protecting group. Examples of particular nitrogen protecting groups include, but are not limited to, tert-butoxycarbonyl. Such compounds are useful in the processes of the invention and provide a suitable material for preparing corresponding 2-methylpyrrolidine compounds.

The compounds and processes described herein will be better understood in connection with the Examples, which are intended as an illustration of and not a limitation upon the scope of the invention.

EXAMPLES

Example 1

Preparation of
2-(R)-methyl-pyrrolidine-1-carboxylic tert-butyl ester (5)

Step 1: Preparation of
2-(S)-hydroxymethyl-pyrrolidine-1-carboxylic acid tert-butyl ester (2)

A solution of (S)-prolinol (1, 50 g, 0.49 mol) in ethyl acetate (250 mL) was cooled to 0° C. Triethylamine (139 mL, 101 g, 1 mol) was added dropwise to this cold reaction mixture while maintaining the reaction temperature at below 0° C. A solution of tert-butoxycarbonyl anhydride (126 mL, 119.7 g, 0.54 mol) in ethyl acetate (100 mL, EtOAc) was added dropwise to the reaction mixture while maintaining reaction temperature below 0° C. (~30 minutes). The reaction mixture was stirred at room temperature overnight (~11 hours). TLC showed absence of starting material (on Si gel, EtOAc, $I_2$). The product was detected by HPLC at 205 nm. Reaction was quenched with 1 M aqueous $H_3PO_4$ (300 mL). The organic layer was separated and washed with 1 M aqueous $H_3PO_4$ (3×300 mL) followed by saturated aqueous $NaHCO_3$ (3×200 mL), dried ($MgSO_4$), filtered and concentrated to leave an oily residual product (109 g, 99.5 g for 100% yield). $^1H$ NMR ($CDCl_3$):δ 1.47 (s, 9H, 3×$CH_3$), 1.81 (m, 2H, $CH_2$), 2.01 (m, 2H, $CH_2$), 3.38 (m, 2H, $CH_2$), 3.61 (m, 2H, $CH_2$) and 3.97 (m, 1H, CH); $[M+H]^+$ at m/z 202.

Step 2: Preparation 2-(S)-methanesulfonyloxymethyl-pyrrolidine-1-carboxylic acid tert-butyl ester (3)

A solution of 2-(S)-hydroxymethyl-pyrrolidine-1-carboxylic acid tert-butyl ester (compound (2) obtained from above, 109 g, 99.5 g for 100% yield, 0.49 mol) in dichloromethane (500 mL) was cooled to 0° C. Triethylamine (139 mL, 101 g, 1 mol) was added to the cold solution dropwise while maintaining the reaction temperature below 0° C. Methanesulfonyl chloride (58 mL, 85.8 g, 0.75 mol) was added dropwise to reaction mixture while maintaining the reaction temperature at below 0° C. (~1 hour). The reaction mixture was stirred at room temperature overnight (~11 hours). HPLC showed absence of starting material. The reaction mixture was quenched with 1 M $H_3PO_4$ (300 mL) and mixed for 15 minutes. The organic layer was separated and washed with 1 M aqueous $H_3PO_4$ (2×300 mL), followed by saturated aqueous $NaHCO_3$ (4×250 mL), dried over $MgSO_4$, filtered, and concentrated to leave an oily residual product (132 g, 95.6% yield). $^1H$ NMR ($CDCl_3$):δ 1.48 (s, 9H, 3×$CH_3$), 1.82–2.08 (m, 4H, 2×$CH_2$), 3.01 (s, 3H, $CH_3$), 3.36 (m, 2H, $CH_2$), 3.944.18 (m, 2H, $CH_2$) and 4.29 (m, 1H CH); $[M+H]^+$ at m/z 280.

Step 3: Preparation of 2-(S)-iodomethyl-pyrrolidine-1-carboxylic acid tert butyl ester (4)

A solution of 2-(S)-methanesulfonyloxymethyl-pyrrolidine-1-carboxylic acid tert-butyl ester (compound (3) obtained from above, 30 g, 0.10 mol) in anhydrous tetrahydrofuran (600 mL) was cooled to 0° C. Lithium iodide (144 g, 1 mol) was added to the cold reaction mixture as a solid in portions while maintaining the reaction temperature at below 30° C. The reaction mixture was warmed to 62° C. until HPLC showed less than 2% starting material. The reaction mixture was quenched with 10% aqueous sodium thiosulfate (300 mL). Ethyl acetate (600 mL) was added to reaction mixture. The organic layer was separated. The aqueous layer was re-extracted with ethyl acetate (3×50 mL). The combined organic layer was washed with brine (2×100 mL), dried over $MgSO_4$, filtered, and concentrated to leave an oily residual product (26.3 g, 78.6% yield). $^1H$ NMR ($CDCl_3$): δ 1.46 (d, 3H, $CH_3$), 1.48 (d, 6H, 2×$CH_3$), 1.792.14 (m, 4H, 2×$CH_2$), 3.14–3.52 (m, 4H, 2×$CH_2$) and 3.88 (m, 1H, CH); $[M+H]^+$ at m/z 312.

Step 4: Preparation of 2-(R)-methyl-pyrrolidine-1-carboxylic tert-butyl ester (5)

A heterogenous reaction mixture of 2-(S)-iodomethyl-pyrrolidine-1-carboxylic acid tert butyl ester (compound (4) obtained from above, 25 g, 0.08 mol), triethylamine (11.2 mL, 8.12 g, 0.08 mol) in methanol (250 mL) and 5% palladium on carbon (2.5 g, 10 wt %, Pd/C) was allowed to react at room temperature under a blanket of hydrogen gas overnight and until HPLC showed less than 1% starting material (~7 hours). The reaction mixture was filtered and the filtrate was concentrated to a residue. The residue was dissolved in distilled water (100 mL) and ethyl acetate (100 mL). The organic layer was separated and the aqueous layer was re-extracted with ethyl acetate (2×50 mL). The combined organic layer was washed with 1 M aqueous $H_3PO_4$ (2×100 mL) followed by saturated $NaHCO_3$ (233 100 mL), dried over $MgSO_4$, filtered, and concentrated to leave an oily residual product (12.78 g, 85.9% yield). $^1H$ NMR ($CDCl_3$): δ 1.16 (d, 3H, $CH_3$), 1.47 (s, 9H, 3×$CH_3$), 1.50–1.82 (m, 2H, $CH_2$), 1.84–2.03 (m, 2H, $CH_2$ ), 3.34 (m, 2H, $CH_2$) and 3.86 (m, 1H, CH); $[M+H]^+$ at m/z 186.

Example 2

Preparation of 2-(R)-methyl-pyrrolidine-1-carboxylic tert-butyl ester (5)

Step 1: Preparation of 2-(S)-methanesulfonyloxymethyl-pyrrolidine-1-carboxylic acid tert-butyl ester (3)

The compound (3) was prepared according to procedures describe above for Example 1, Steps 1–2.

Step 2: Preparation of 2-(R)-methyl-pyrrolidine-1-carboxylic tert-butyl ester (5)

A solution of 2-(S)-methanesulfonyloxymethyl-pyrrolidine-1-carboxylic acid tert-butyl ester (compound (3), 4.6 g, 0.016 mol) in anhydrous tetrahydrofuran (50 mL, THF) was cooled to 0° C. 1.0 M Lithium triethylborohydride in THF (38 mL, 3.17 g, 0.029 mol) was added dropwise to the reaction mixture while maintaining reaction temperature below 0° C. The reaction mixture was refluxed for overnight (~11 hour). HPLC showed absence of starting material. Reaction mixture was cooled to 0° C. and ethyl acetate (50 mL) was slowly added followed by addition of distilled water (50 mL) while maintaining temperature below 10° C. The organic layer was separated and washed with distilled water (2×50 mL), 1 M $H_3PO_4$ (2×50 mL) and saturated $NaHCO_3$ (2×50 mL), dried over $MgSO_4$, filtered, and concentrated to leave an oily residual product (2.46 g, 53.5% yield). $^1H$ NMR ($CDCl_3$): δ 1.16 (d, 3H, $CH_3$), 1.47 (s, 9H, 3×$CH_3$), 1.50–1.82 (m, 2H, $CH_2$), 1.84–2.03 (m, 2H, $CH_2$), and 3.86 (m, 1H, CH).

Example 3

Preparation of 2-(S)-methyl-pyrrolidine-1-carboxylic tert-butyl ester (5)

Step 1: Preparation of 2-(R)-hydroxymethyl-pyrrolidine-1-carboxylic acid tert-butyl ester (2)

The 2-(R)-hydroxymethyl-pyrrolidine-1-carboxylic acid tert-butyl ester was prepared according to the procedures described for Example 1, Step 1, except substituting (R)-prolinol for (S)-prolinol.

Step 2: Preparation of 2-(R)-(toluene-4-sulfonyloxymethyl)-pyrrolidine-1-carboxylic acid tert-butyl ester (3)

To a well-stirred solution of 2-(R)-hydroxymethyl-pyrrolidine-1-carboxylic acid tert-butyl ester (compound (2), 15 g, 75 mmol) in 42 mL of pyridine and 100 mL of dichloromethane at 0° C. was added a solution of 4toluenesulfonyl chloride (15.68 g, 82.55 mmol) in 75 mL of dichloromethane in a dropwise manner while maintaining the reaction temperature below 0° C. After the addition was complete, the temperature of the reaction was allowed to rise to ambient temperature (~23° C.) and the reaction was stirred for 5 hours, at which time another 5 grams of 4-toluenesulfonyl chloride was added. The reaction was stirred for 15 hours. The reaction mixture was poured into 150 mL of a 2:1 mixture of dichloromethane and hexane. The mixture was washed twice with a mixture of 100 mL of saturated $NaH_2PO_4$ (pH=4.1) solution and water, and then washed with 500 mL of a mixture of 100 mL of $Na_2HPO_4$ and water. The organic phase was dried over anhydrous sodium sulfate, concentrated in vacuo, and purified by flash chromatography, eluting with 15% EtOAc in hexane to give a clear oil (22.9 g, 86% yield).

Step 3: Preparation of 2-(S)-methyl-pyrrolidine-1-carboxylic tert-butyl ester (5)

To a solution of 2-(S)-(toluene-4-sulfonyloxymethyl)-pyrrolidine-1-carboxylic acid tert-butyl ester (compound (4), 1.77 g, 4.99 mmol) in 5 mL of THF at 0° C. was added dropwise 15 mL (15 mmol) of a 1 M THF solution of lithium triethylborohydride. After 15 hours, the reaction was quenched by addition of 7.39 mL of water. The reaction was diluted with 35 mL of chloroform, and poured into a separatory funnel. The mixture was diluted with dichloromethane and washed with saturated aqueous NaCl solution. The organic phase then was dried over sodium sulfate. The mixture was concentrated in vacuo and purified by flash chromatography on silica gel, eluting with 1:3 ethyl acetate/hexane to give pure product as a clear oil (0.73 g, 79% yield).

Example 4

Preparation of 2-(R)-methyl-pyrrolidine.HCl (6)

2-(R)-Methyl-pyrrolidine-1-carboxylic tert-butyl ester (compound (5), 12 g, 64 mmol), obtained from Example 1, Step 4, was dissolved in ethyl acetate and HCl gas was passed through it for 5 minutes until the pH of the reaction mixture was below 1. The reaction mixture was mixed at room temperature for 2 hours. HPLC showed the absence of the starting material. The reaction mixture was concentrated to leave a residue, which was triturated with methyl tert-butyl ether (3×30 mL) while decanting the liquors. The hygroscopic solid was dried at 40° C. overnight with nitrogen bleeding to give a white solid product as HCl salt (7.5 g, 95.6% yield). $^1$H NMR ($CDCl_3$): δ 1.55 (d, 6H, 233 $CH_3$), 1.66–2.05 (m, 2H, $CH_2$), 2.13 (m, 2H, $CH_2$), 3.37 (m, 2H, $CH_2$) and 3.70 (m, 1H, CH); $[M+H]^+$ at m/z 122.

Various changes and modifications to the disclosed embodiments will be apparent to those skilled in the art. Such changes and modifications are within the purview of the invention and can be made without departing from the spirit and scope thereof, which is defined by the appended claims.

What is claimed is:
1. A process for preparing a compound of formula (V):

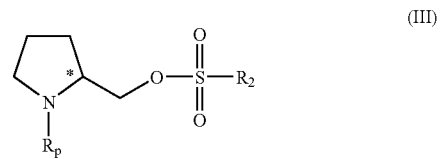

wherein $R_1$ is hydrogen or a nitrogen-protecting group, or a salt thereof, comprising the steps of:
  4a) providing a compound of formula (III):

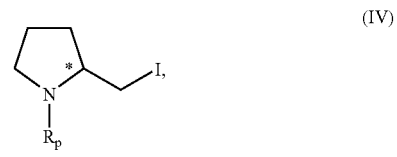

wherein * denotes a chiral center that can be designated as a R— or S-stereocenter, $R_p$ is a nitrogen-protecting group, and $R_2$ is an unsubstituted alkyl, substituted alkyl, unsubstituted aryl, or substituted aryl group, and treating the compound of formula (III) with an alkali metal iodide salt to obtain a compound of the formula (IV):

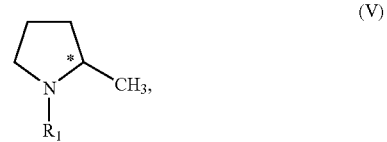

wherein * and $R_p$ are as defined for a compound of formula (III); and
  4b) hydrogenating a compound of formula (IV) to obtain a desired enantiomer of a compound of formula (V):

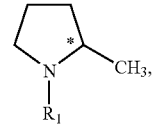

wherein * and $R_1$ are as previously defined.
2. The process according to claim 1, wherein step 4a) is substituted with a step comprising reacting a compound of formula (II):

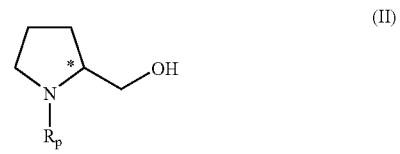

wherein * is as previously defined and $R_p$ is a nitrogen-protecting group, with an iodine reagent to obtain a compound of formula (IV).

* * * * *